(12) United States Patent
Matsui

(10) Patent No.: US 6,669,629 B2
(45) Date of Patent: Dec. 30, 2003

(54) ENDOSCOPE SYSTEM COMPRISING AN ELECTRICALLY BENDABLE ENDOSCOPE

(75) Inventor: Koichi Matsui, Koganei (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/128,891

(22) Filed: Apr. 24, 2002

(65) Prior Publication Data

US 2002/0165432 A1 Nov. 7, 2002

(30) Foreign Application Priority Data

Apr. 24, 2001 (JP) .......................... 2001-126230
Apr. 24, 2001 (JP) .......................... 2001-126232

(51) Int. Cl.[7] ................................................ A61B 1/01
(52) U.S. Cl. ...................... 600/152; 600/145; 600/146; 600/102
(58) Field of Search ................................ 600/152, 149, 600/146, 102, 118, 145

(56) References Cited

U.S. PATENT DOCUMENTS

| 4,286,585 A | * | 9/1981 | Ogawa | 600/145 |
|---|---|---|---|---|
| 4,941,454 A | | 7/1990 | Wood et al. | |
| 5,159,446 A | * | 10/1992 | Hibino et al. | 348/65 |
| 5,400,769 A | * | 3/1995 | Tanii et al. | 600/152 |
| 6,371,907 B1 | * | 4/2002 | Hasegawa et al. | 600/146 |
| 6,551,237 B2 | * | 4/2003 | Matsui | 600/118 |

* cited by examiner

Primary Examiner—John P. Leubecker
(74) Attorney, Agent, or Firm—Scully, Scott, Murphy & Presser

(57) ABSTRACT

The endoscope system comprises a endoscope in which a bendable portion is motor bendable; an operation switch for giving an instruction as to a bending amount; a motor for bending the bendable portion in accordance with a bending instruction signal; a detection portion for detecting the bent state of the bendable portion; a first driving power generating portion which generates power for driving the motor in accordance with a difference between an instructed bending amount fed via the operation switch and a value representing the bending state of the bending portion and given by the detection portion; a second driving power generating portion for generating a pulse driving power having a predetermined magnitude; and a control portion whose control includes selecting one of the first and second driving power generating means depending on said difference, and causing the thus selected means to drive motor so as to bend the bendable portion.

6 Claims, 9 Drawing Sheets

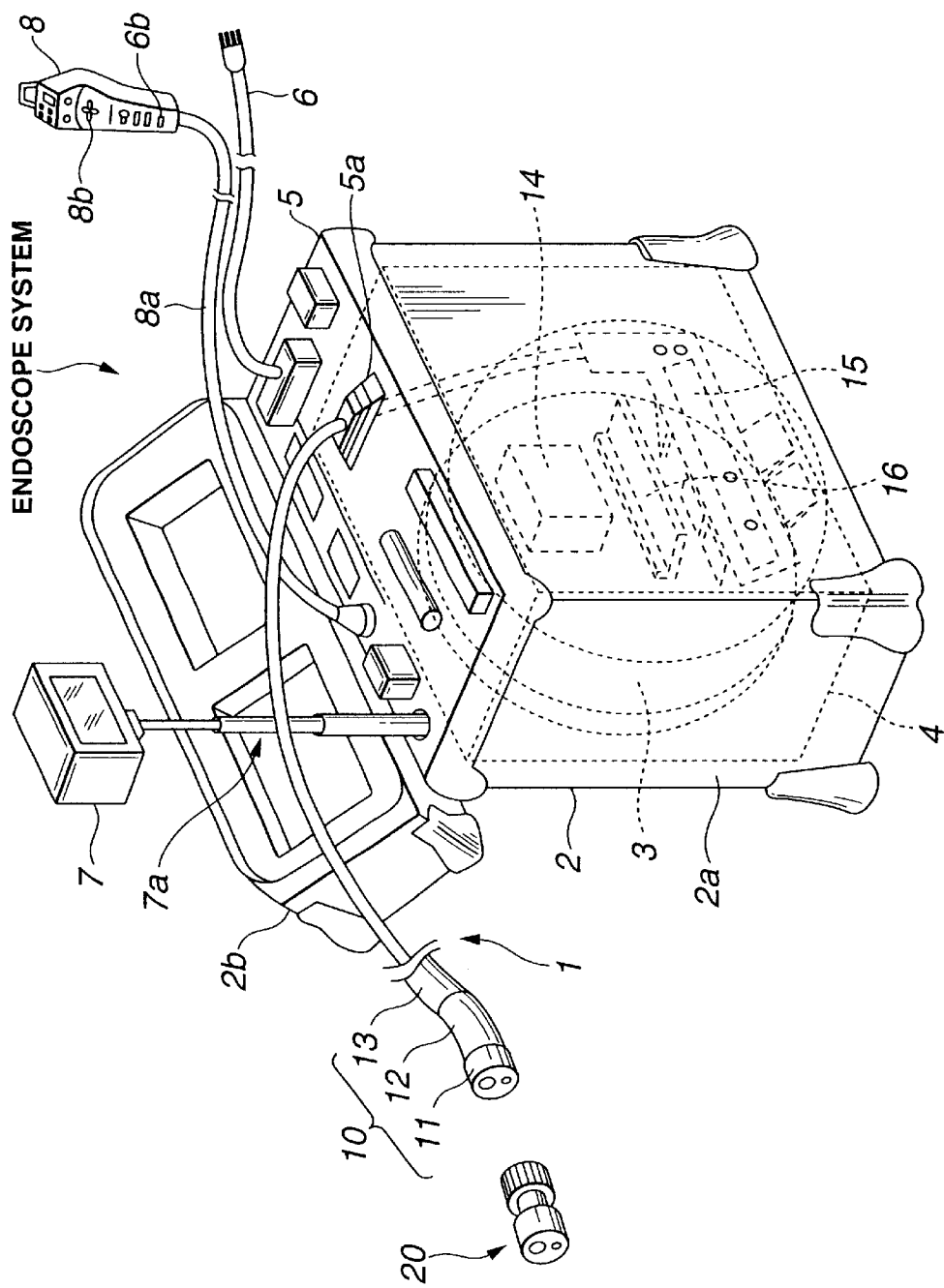

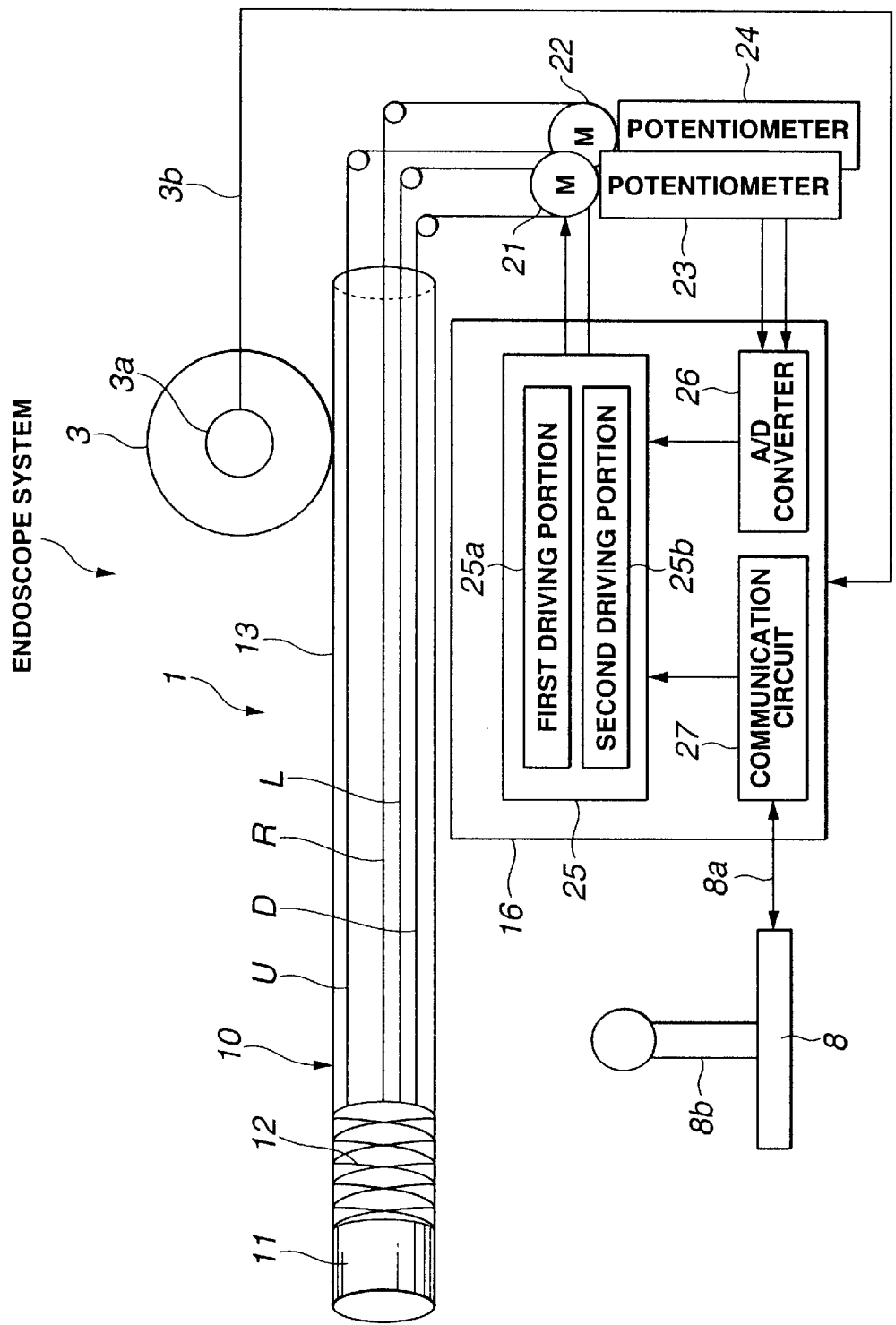

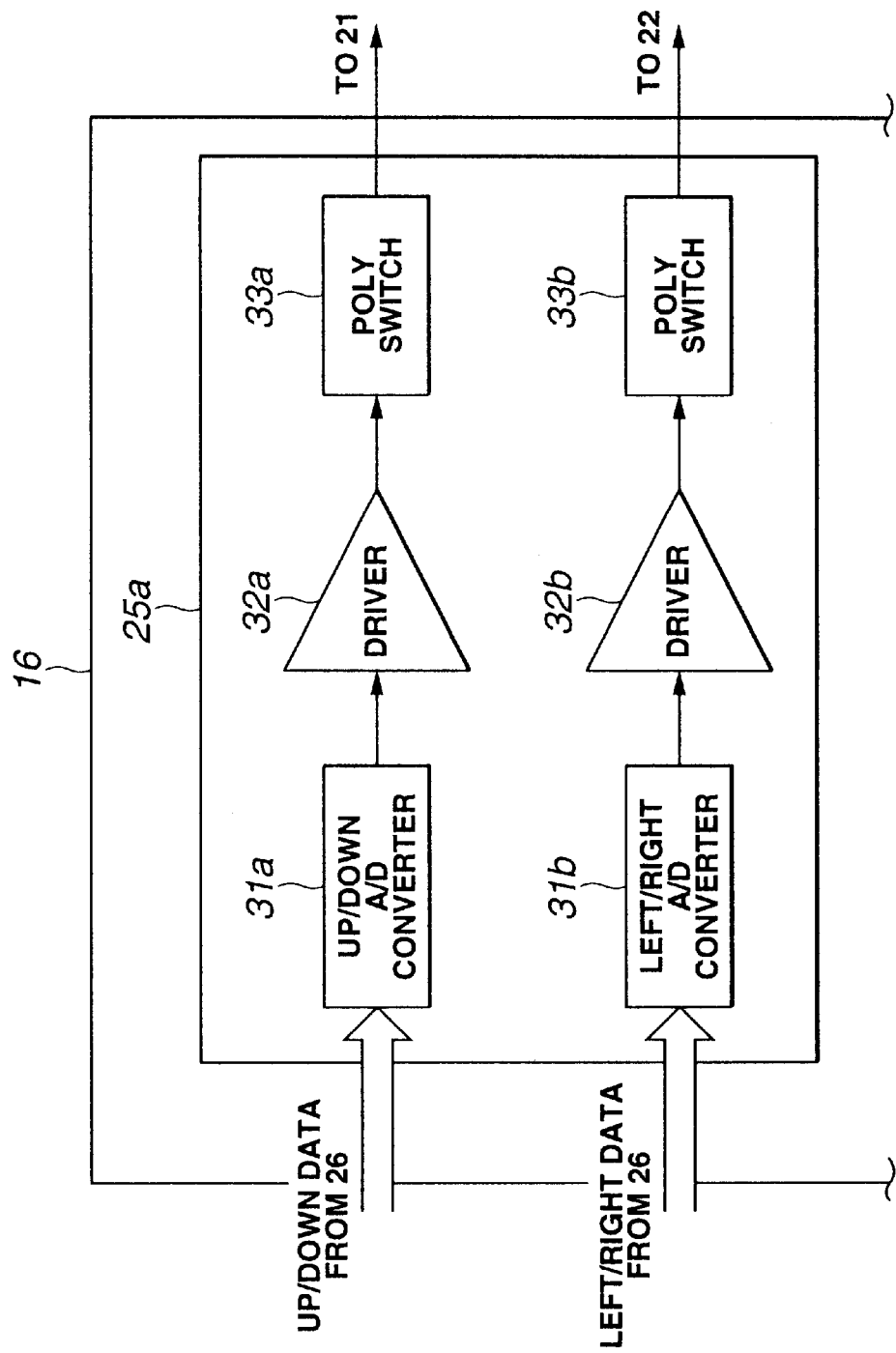

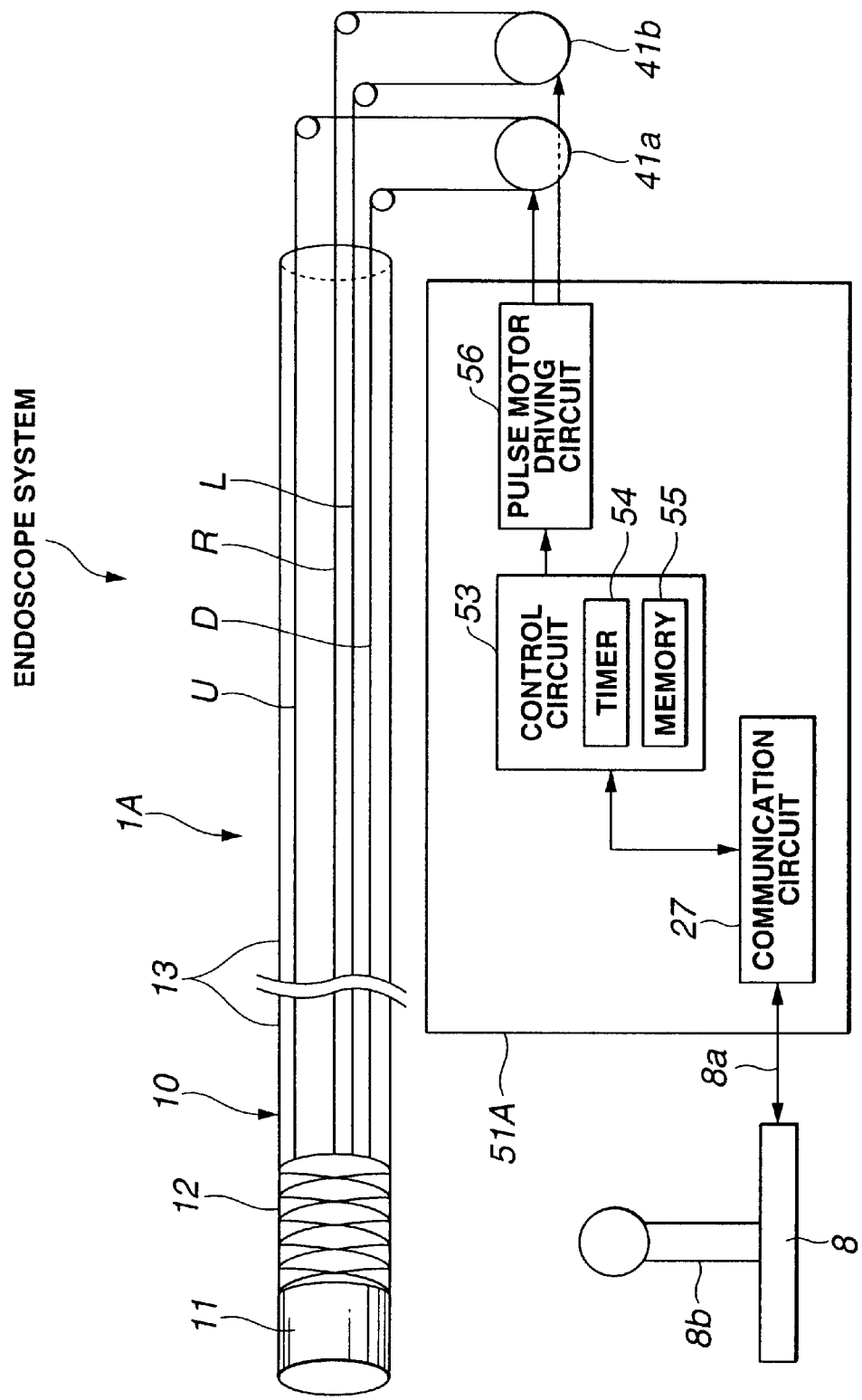

US 6,669,629 B2

ENDOSCOPE SYSTEM COMPRISING AN ELECTRICALLY BENDABLE ENDOSCOPE

This application claims benefit of Japanese Application Nos. 2001-126230 filed on Apr. 24, 2001 and 2001-126232 filed on Apr. 24, 2001, the content of which is incorporated by this reference.

BACKGROUND OF THE INVENTION

1. Field of the Invention

The present invention relates to an endoscope system comprising an electrically bendable endoscope whose bendable portion is bent via a driving force from driving means, and a bending driving control unit for controlling the driving means.

2. Description of the Related Art

Recently, endoscopes are widely used in the medical field. It is possible to observe a site in a bodily cavity and to apply various treatments on the site by inserting a slender insertion portion of the endoscope into the bodily cavity.

Endoscopes are also used in industrial fields. With the endoscope used in these fields, its insertion portion is inserted into the interior of a boiler, engine, etc., to observe or fix a site.

Generally, the tip end of the insertion portion of such an endoscope includes a bendable portion where is bendable upwards or downward, or leftward or rightward. Inclusion of such bendable portion not only makes it possible for the tip end to more easily pass through a tortuous channel, but also for an optical system attached to the tip end to be more readily directed towards a site to be observed, which will ensure good observation. Bending the bendable portion has been achieved manually or by utilizing a force brought about by a bending motor (to be referred to simply as motor hereinafter).

Among so-called electrically bendable endoscopes (hereinafter referred to as electric endoscope) in which the bendable portion is bent via a force from a motor, some have a joystick in its operation portion as an input feeding means. According to this type of electric endoscopes, the operator instructs the system as to the direction and amount of bending by manipulating the joystick, and the motor is driven according to this instruction. Then, bending effecting wires connected to the bendable portion are pulled, thereby bending the bendable portion in the instructed direction.

According to this electric endoscope, a driving voltage applied to the motor is controlled based on the difference between an instructed bending amount transmitted via the joystick and a value indicated by a potentiometer representing the actual bending amount of the tip end.

Because of this, if the instructed bending amount given via the joystick and the value detected by the potentiometer are very close to each other, a driving force from the motor becomes so small that delicate displacement of the tip end would become impossible.

Further, if the electric endoscope has a long insertion portion to be wound around a drum, and the driving voltage applied to the motor is controlled based on said difference, the bending angle of the bendable portion would vary depending on whether the bending portion is wound around the drum or drawn out from the drum, even if the same bending amount was instructed via the joystick.

Furthermore, with the electric endoscope incorporating a motor-based bending control unit in which instruction regarding a bending amount fed by a bending input feeding means such as a joystick is captured without delay so that the bending amount may serve as a direct reference according to which the motor is controlled to give a desired bending angle, as disclosed, for example, in the U.S. Pat. No. 4,941,454, small fluctuations in the input from the input feeding means will cause the bendable portion to undergo corresponding fluctuated bending. In addition, with this motor-based bending control unit, if there is a difference between the bending amount fed via the bending input feeding means and the actual bent angle of the bendable portion, and the difference is large, the motor might generate a too large force, thereby exposing the bending effecting wire to a too large strain, all the more because the motor is controlled so as to drive and reduce the difference.

SUMMARY OF THE INVENTION

An object of the present invention is to provide an endoscope system in which it is possible to securely direct the tip end of an electrically bendable endoscope towards a target site by precisely controlling a driving force applied to a bendable portion of the electrically bendable endoscope.

Another object of the present invention is to provide an endoscope system in which it is possible to reduce strains imposed on bending effecting wires of an electrically bendable endoscope.

The endoscope system of the present invention comprises an electrically bendable endoscope; bending input feeding means for giving an instruction as to a bending amount which includes a bending direction and a bending position; driving means for bending a bendable portion in accordance with a bending instruction signal; detection means for detecting a bent state of the bendable portion; first driving power generating means for generating power necessary for driving the driving means responsible for bending the bendable portion in accordance with a difference between the bending amount instructed via the bending input feeding means and a value given by the detection means representing a bent state of the bendable portion; second driving power generating means for generating pulse driving powers having a predetermined magnitude; and control means for selecting either the first or the second driving power generating means depending on said difference, and driving the driving means using the power therefrom, thereby controlling the bending of the bendable portion. Thus, this system in which the control means controls the action of the driving means based on said difference will ensure that an optimum driving power is selected to operate the driving means.

The above and other objects, features and advantages of the invention will become more clearly understood from the following description based on the accompanying drawings.

BRIEF DESCRIPTION OF THE DRAWINGS

FIGS. 1 to 7 illustrate a first embodiment of this invention:

FIG. 1 illustrates the composition of an endoscope system comprising an electrically bendable endoscope;

FIG. 2 illustrates the compositions of a bending mechanism and of a control unit of the electrically bendable endoscope;

FIG. 3 illustrates the composition of a first driving portion;

FIG. 5 illustrates the driving voltage as a function of the control time;

FIG. 6 illustrates the pulse driving voltage as a function of the control time; and FIG. 7 illustrates the pulse driving voltage with finely adjustable driving voltages added, as a function of the control time.

FIG. 9 illustrates another composition of the bending mechanism and control unit of the electrically bendable endoscope; and FIG. 10 is a flowchart to show the flow of control steps.

FIG. 11 illustrates a still other composition of the bending mechanism and control unit of the electrically bendable endoscope.

DETAILED DESCRIPTION OF PREFERRED EMBODIMENTS

Figure 4A:
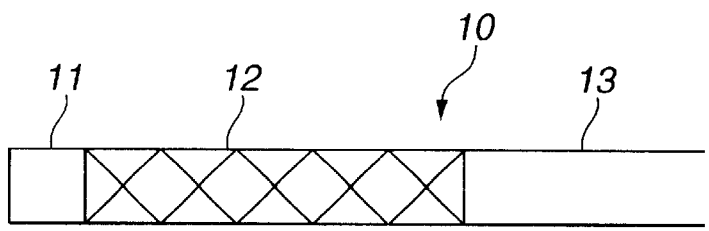
FIG. 4A shows a bendable portion kept straight.

A first embodiment of the present invention will be described with reference to FIGS. 1 to 7.

As shown in FIG. 1, the endoscope system of this invention is principally constituted of an electrically bendable endoscope 1 (to be abridged as endoscope hereinafter), and a housing case 2 to house the endoscope 1. The housing case 2 is principally constituted of a box body 2a and a lid body 2b, and includes buffer materials and others for moderating mechanical shocks that might be inflicted on equipment within.

The endoscope 1 is an endoscope for industrial use having a flexible, slender insertion portion 10. The insertion portion 10 can be withdrawn to be wound around the external surface of a drum 3 in the box body 2a which serves as a winding means. The drum portion 3 is rotatably attached to a frame portion 4 fitted to the box body 2a.

A front panel 5 is attached to the top of the frame portion 4. The front panel 5 carries various switches and connectors, and supply-and-exhaust ducts on its surface. The front panel 5 also carries an AC cable 6 capable of providing the system with power from a commercial power source, and a monitor 7 freely rotatably attached to the top of a stand 7a which can freely elongate or contract. There is provided a remote controller 8 which is capable of being freely connected to or disconnected from the front panel 5 via a cable 8a.

An insertion portion 10 of the endoscope 1 extends from the front panel 5 externally through a rubber member 5a which is installed for preventing the segment in question from being unduly bent due to its own weight. The insertion portion 10 comprises, from its tip end in order, a rigid tip end 11, a bendable portion 12 capable of being freely bent upwards or downwards, and a slender, flexible tube portion 13. In order to bend the tip end 11 in a desired direction, it is necessary to manipulate a joystick 8b which serves as bending input feeding means of the remote controller 8. Through this manipulation, the bendable portion 12 undergoes bending.

The drum portion 3 comprises, in its interior, a camera control unit 14, electrical bending unit 15, electrical bending control unit 16 (hereinafter, referred to as control unit), etc.

The camera control unit 14 is provided with a light source portion which transmits illuminating light to a light guide (not illustrated here) serving as an illumination light transmitting means for the endoscope 1, and with a signal processing portion for processing signals from an image pickup element (not illustrated here) installed in the tip end 11. The electrical bending unit 15 comprises a driving mechanism for bending the bendable portion 12. The control unit 16 controls the operation of the electrical bending unit 15.

The joystick 8b of the remote controller 8 determines the bending of the bendable portion 12 by giving an instruction as to a bending amount which includes a bending direction and bending position. The instruction signal from the joystick 8b is fed to the control unit 16.

Incidentally, various optical adapters 20 can be freely attached to or detached from the tip end 11 of the insertion portion 10, so as to alter the optical characteristics such as the visual direction, visual angle, etc.

As shown in FIG. 2, the insertion portion 10 comprises, in its interior, an upward bending wire U (up wire) for bending the bendable portion 12 upward to cause the visual field to turn upward; a downward bending wire D (down wire) to cause the visual field to turn downward; a rightward bending wire R (right wire) to cause the visual field to turn rightward; and a leftward bending wire L (left wire) to cause the visual field to turn leftward.

The proximal ends of the upward and downward bending wires U and D are connected to an upward/downward bending motor 21 (up/down motor) which serves as driving means for the bendable portion 12, while the proximal ends of the rightward and leftward bending wires R and L are connected to a leftward/rightward bending motor 22 (left/right motor). The wires U, D, R and L are restricted in their traveling distance by stoppers not illustrated here.

To the up/down motor 21, is co-axially attached an up/down potentiometer 23 which serves as a means for determining a bending amount of the bendable portion 12 by detecting a bending angle of that portion. Also to the left/right motor 22, is co-axially attached a left/right potentiometer 24 which serves as a similar detection means. Moreover, to the drum 3 is co-axially attached a winding detection unit 3a (hereinafter, described as a detection unit) which serves as a detection means for determining a wound-up amount of the insertion portion 10.

The control unit 16 comprises a motor control unit 25 equipped with first and second driving units 25a and 25b both of which serve as driving voltage generating means described later, an A/D converter 26, and a communication circuit 27.

The first and second driving units 25a and 25b of the motor control unit 25 are electrically connected to the up/down and left/right motors 21 and 22, respectively. To the A/D converter 26 are electrically connected the up/down and left/right potentiometers 23 and 24. The A/D converter converts actual bent states of the bendable portion 12 detected by the potentiometers 23 and 24 and expressed in analog amounts into corresponding digital amounts. The communication circuit 27 is electrically connected to the remote controller 8. The communication circuit 27 receives signals such as a digital signal indicating a bending amount fed via the joystick 8b of the remote controller 8.

Incidentally, a symbol 3b represents a signal line for electrically connecting the winding detection unit 3a to the control unit 16.

As shown in FIG. 3, the first driving portion 25a to serve as the first power generating means of the motor control unit 25 comprises, in its interior, an up/down A/D converter 31a for up/down bending, a driver 32a, and a poly switch 33a, and a left/right A/D converter 31b for left/right bending, a driver 32b, and a poly switch 33b. Through this arrangement, in this embodiment, driving voltages provided by the drivers 32a and 32b are delivered via the poly switches 33a and 33b to the motors 21 and 22.

Now, how to operate the endoscope system comprising a motor control unit 25 solely dependent on the first driving portion 25a will be described.

Firstly, the user holds the insertion portion 10 in which the bendable portion 12 is not bent, and inserts the tip end 11 into a hollow test tube towards a site to be observed. During this operation, the operator manipulates the joystick 8b as appropriate, thereby bending the bendable portion 12 to direct the tip end 11 upward, downward, leftward or rightward so as to completely visualize the target site.

During this operation, an bending instruction signal provided via the joystick 8b is fed via the cable 8a to the communication circuit 27. In accordance with the bending instruction signal fed to the communication circuit 27, the motor control unit 25 delivers driving voltages to the up/down and left/right motors 21 and 22.

Then, because the up/down and left/right motors 21 and 22 are put into activation, the upward, downward, rightward and leftward bending wires U, D, R and L are pulled in association to bend the bendable portion 12.

Figure 4B:
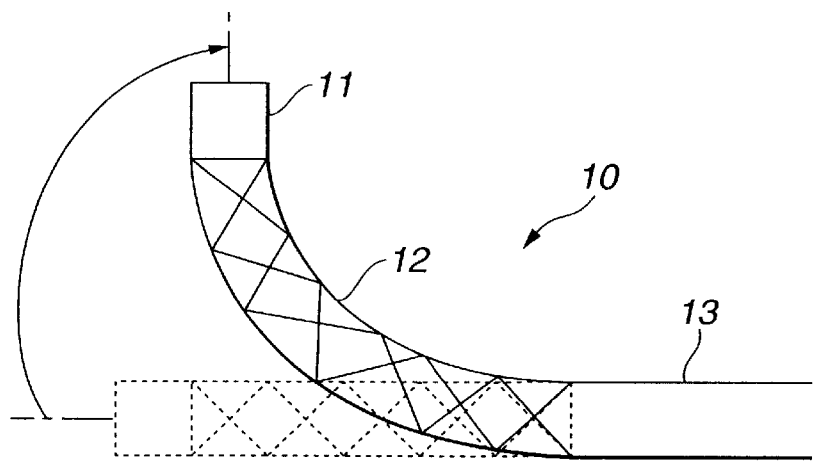
FIG. 4B shows the bendable portion being bent.

Specifically, if it is required to direct the visual field, for example, upward, when the tip end 11 is kept straight as shown in FIG. 4A, the joystick 8b is manipulated so as to cause the bendable portion 12 to be bent upward: the up/down motor 21 is activated to pull the upward bending wire U; the bendable portion 12 switches from a position as represented by dotted lines to a position as represented by solid lines shown in FIG. 4B; and the tip end 11 is displaced upwards of the visual field.

Similarly, it is possible to direct the tip end 11 downward, or rightward or leftward by activating the up/down motor 21 or the left/right motor 22, thereby pulling the downward bending wire D, or the leftward or rightward bending wire L or R, in accordance with respective bending instruction signals.

When the bendable portion 12 is bent, the up/down potentiometer 23 and left/right potentiometer 24 deliver detection signals indicating the rotation angles of the up/down and left/right motors 21 and 22, to the A/D converter 26. Because the system can determine a bending amount of the bendable portion 12 based on the bending angle thus detected, it can achieve a feedback control for the adjustment of the pulls applied to the wires U, D, R and L, thereby making it possible to properly direct the tip end 11 towards a site to be observed.

Now, how the upward/downward bending is controlled will be described for illustration. The leftward/rightward bending is the same with the upward/downward bending, except that the involved members are different, and thus the description of the leftward/rightward bending will be omitted.

A voltage to be delivered to the up/down motor 21 is determined based on a difference between an up/down bending instruction signal representing a bending amount to be introduced and provided to the communication circuit 27 via the joystick 8b, and a digital value representing an actual bending state obtained by feeding output from the up/down potentiometer 23 co-axially attached to the up/down motor 21 to the A/D converter 26 for A/D conversion, and the voltage is applied via the first driving portion 25a to the motor in question.

If the difference between the instructed bending amount fed via the joystick 8b and the digital value representing the actual bent state obtained via the up/down potentiometer 23 is larger than a predetermined value, the voltage to be applied via the first driving portion 25a to the up/down motor 21 is elevated. This causes the up/down motor 21 to rotate at a higher speed.

On the contrary, if the difference in question is smaller than the predetermined value, the voltage to be applied via the first driving portion 25a to the up/down motor 21 is lowered. This causes the up/down motor 21 to rotate at a lower speed.

When the instructed bending amount and the digital value finally become equal, the voltage to be applied to the up/down motor 21 is made null. In other words, when the tip end 11 is far apart from a site to be observed, a high voltage is applied to the up/down motor 21 for driving so that the tip end can radically change bent shape of the bendable portion 12. In contrast, when the tip end 11 is positioned close to the site to be observed, a low voltage is applied to the up/down motor 21 for driving so that the tip end 11 can moderately change bent shape of the bendable portion 12.

Figure 5:
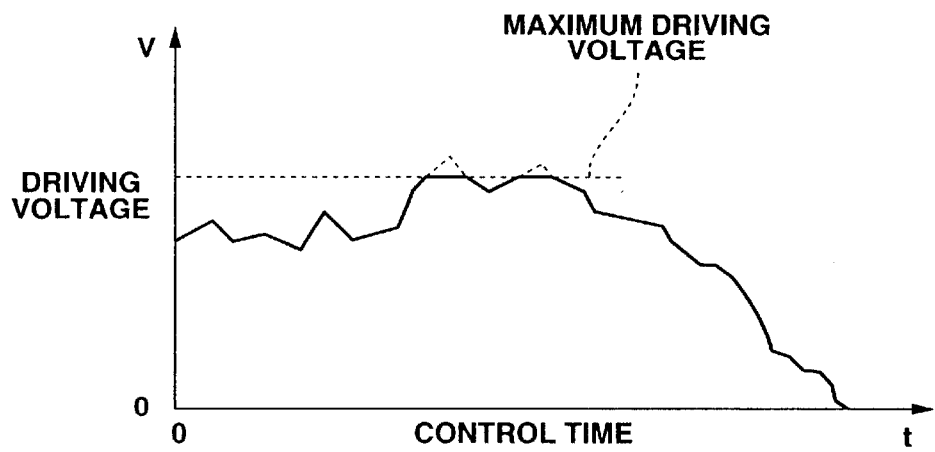

Thus, when the tip end 11 is positioned close to a site to be observed, the voltage applied to the up/down motor 21 becomes zero or close to zero as shown in FIG. 5. Then, there is no sufficiently high voltage available to activate the up/down motor. In this case, it is hardly possible to activate the up/down motor 21 sufficiently to pull the upward or downward bending wire U or D.

Figure 6:
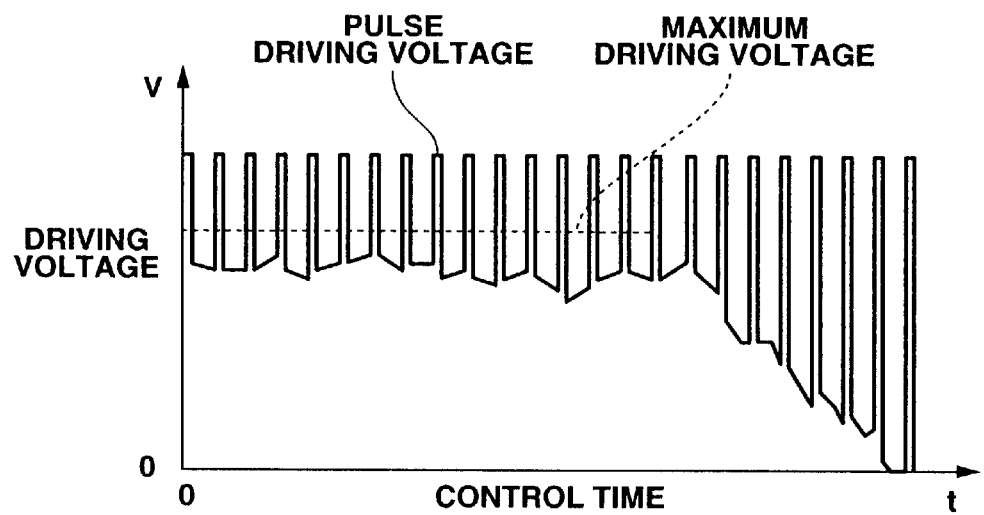

To prevent the occurrence of such inconvenience, in the present embodiment, the motor control unit 25 comprises, in addition to the first driving unit 25a, a second driving unit 25b to serve as a second driving force generating means which applies pulse driving voltages having a predetermined height to the up/down motor 21 as shown in FIG. 6.

The second driving portion 25b applies pulse driving voltages to the up/down motor 21 when the tip end 11 is close to a site to be observed. Driving the up/down motor 21 by applying such pulse driving voltages thereto enables the bendable portion 12 to delicately alter its bent shape. Namely, it becomes possible for the tip end 11 to be delicately displaced until it is properly placed opposite to the site to be observed.

The driving voltage applied via the first driving unit 25a of the motor control unit 25 to the up/down motor 21 is determined in accordance with the aforementioned difference. However, in order to prevent the breakage of the wire U or D suddenly imposed a strain, the maximum acceptable voltage is determined in advance as shown by the broken line of FIG. 5. Because of this, no matter how much said difference exceeds the predetermined level, any driving voltage exceeding the maximum acceptable voltage marked by the broken line is prohibited from being applied to the up/down motor 21.

In contrast, the pulse driving voltages delivered by the second driving unit 25b of FIG. 6 are allowed to attain levels higher than the maximum acceptable voltage marked by the broken line of FIG. 5. This is because in this case the driving voltage occurs as pulse voltages repeating at intervals, and the wire U or D will never break even if exposed to such driving voltages whose height exceeds the maximum acceptable level, as long as the driving voltages occur as pulse driving voltages.

As discussed above, it is possible to quickly direct the tip end towards a site to be observed, by controlling the driving voltages delivered by the first driving unit to the bending motors in accordance with the difference between the bending instruction signal indicating a desired bending amount fed via the joystick, and a digital value obtained from the potentiometer representing the current bent state.

If the difference between the bending instruction signal and the digital value is smaller than the predetermined value, suggesting that the tip end is close to the site to be observed, the system causes the second driving portion to deliver pulse driving voltages to the involved bending motor, thereby enabling the tip end to delicately alter its position, so as to be precisely directed towards the site to be observed.

In this embodiment, the bending input feeding means for feeding a bending instruction signal consists of a joystick. However, the bending input feeding means need not to be limited to a joystick, but may include operation switches based on other mechanisms. Further, in the above embodiment, the height of pulse driving voltages is set at a constant level. However, the substantial alteration of individual pulse driving voltages will not interfere with the normal operation of the embodiment.

Incidentally, according to the present endoscope system embodying the invention, if the site to be observed is close to the user, the insertion portion 10 does not necessarily need to remain long. In such a case, the proximal end of the insertion portion 10 is wound around the drum 3. This will improve the easiness with which the operator handles the system.

However, if the insertion portion 10 is withdrawn and its proximal end is wound around the drum 3, the wires U, D, R and L will change their positions relative to each other in the insertion portion 10. Because of this, even if the detection value obtained from the up/down potentiometer 23 or from the left/right potentiometer 24 is the same with the corresponding value obtained when the insertion portion has its entire length drawn out, the actual bending angle will be smaller than the counterpart obtained in the latter normal condition.

To meet this situation, according to this embodiment, voltages applied by the motor control unit 25 of the control unit 16 to the motors 21 and 22 are corrected according to an output value from the detection unit 3a attached to the drum 3.

Specifically, if the output value from the detection unit 3a is large, the correction applied to the driving voltage will become large. Namely, if the insertion portion 10 is withdrawn and its proximal end is wound around the drum 3, the detection value from the up/down potentiometer 23 or from the left/right potentiometer 24 is made larger than normal, thereby correcting the positions of the wires U, D, R and L relative to each other.

Through this arrangement it is possible to keep the bending angle of the bendable portion 12 practically the same whether the insertion portion takes a position at which output from the detection unit 3a takes a value suggesting the rotation amount to be zero, or takes another position at which output from the detection unit 3a takes a value suggesting the rotation amount to be one.

The method how to calculate the correction value will be described below.

$$V\_lp = k*Drum + V\_st*(Joy-Pot)$$

where

V_lp: corrected voltage value according to the wound-up amount of the insertion portion around the drum;

k: correction factor dependent on the drum condition;

Drum: value indicating the loop condition (when the insertion portion is kept straight, the value is zero);

V_st: voltage factor when the insertion portion is kept straight;

Joy: instruction value fed via joystick; and

Pot: output value from the potentiometer.

Figure 7:
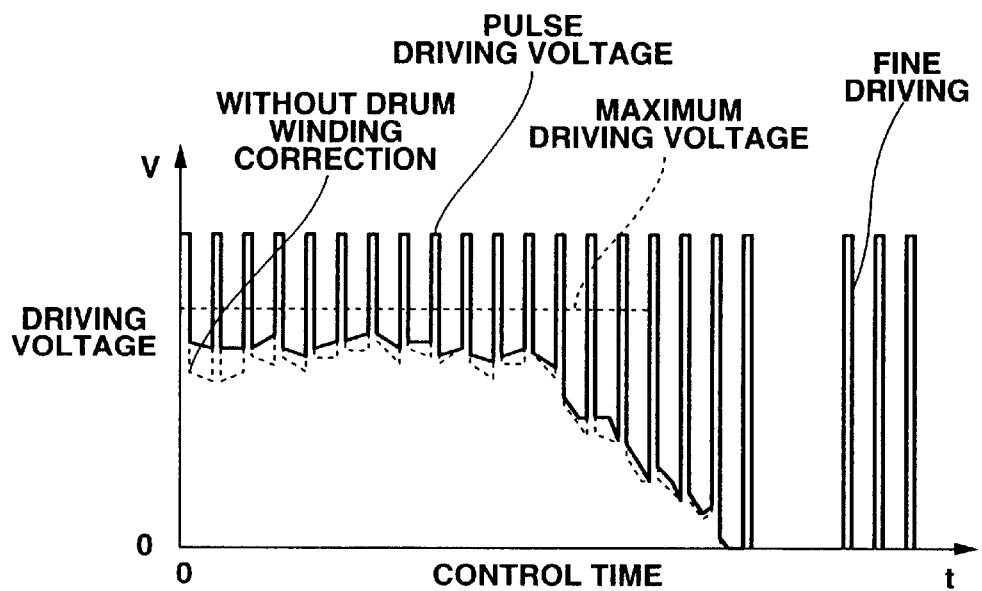

Pulse driving voltages corresponding to the V_lp value obtained from the above equation are applied by the motor control unit 25 to the up/down motor 21 as shown in FIG. 7. The V_lp voltage is restrained so as not to exceed a certain voltage value which, if applied, could break the wire U, D, R or L. Because the driving voltage occurs as pulse driving voltages, breakage of the wire U, D, R or L due to that voltage will be safely prevented, even if the voltage exceeds the maximum acceptable voltage.

The correction to compensate for the error of the bending angle associated with the amount wound by the drum 3 of the insertion portion 10 need not to occur in terms of the voltage value V_lp. Correction in terms of the height of the pulse driving voltage will give the same effect.

Moreover, if the insertion portion 10 is withdrawn and its proximal end is wound around the drum 3, a pulling force applied to the wire U, D, R or L to bend the insertion portion 10 by a given bending angle will be larger than the corresponding force required to produce the same bending angle when the bendable portion 12 is kept straight. In worst cases, the increased pulling force might result in the breakage of the wire U, D, R or L. To avoid this, a tolerable number of turns of the insertion portion 10 around the drum 3 is determined in advance, and if the turns of the bendable portion 12 around the drum exceeds the predetermined number, the bending angle the bendable portion 12 will take is decreased in association. This protects the wires U, D, R and L against breakage.

As discussed above, because the driving voltage determined by the difference between the bending instruction signal and the digital value is corrected in accordance with the amount wound by the drum of the insertion portion, it is possible to ensure a constant bending amount regardless of the amount wound by the drum of the insertion portion.

Further, it is possible to protect the bending wire against breakage by restraining a bending amount if the driving voltage exceeds a predetermined value, as well as by correcting the driving voltage determined by said difference according to the length wound by the drum of the insertion portion.

According to this embodiment, the correction of the driving voltage is introduced to increase the voltage in accordance with the number of turns of the insertion portion around the drum. However, the correction may decrease the voltage in accordance with the number of turns of the insertion portion around the drum.

Alternatively, although this embodiment includes potentiometers, the same control can be achieved by substituting the potentiometers for encoders.

Still further, because it is possible to displace the tip end 11 bit by bit by rendering the voltage value V_lp to zero, and applying only pulse voltages to the motor, bending of the bendable portion 12 is finely adjusted.

Still further, even if the control unit 16 happens to become so unstable in its operation as to completely lose its control, the wires U, D, R and L will be forcibly arrested by the stopper so that the bendable portion 12 is safely prevented from being excessively bent.

If the wires U and D, or R and L are arrested by the stopper, a driving voltage will be applied to the up/down motor 21 or to the left/right motor 22 in accordance with a detection value from the A/D converter 31a or 31b, to cause an excessively large current to flow through the up/down motor 21 or through the left/right motor 22. The excessively large current flowing through the up/down motor 21 or through the left/right motor 22 will also pass through a poly switch 33a or 33b inserted between the driver 32a and the up/down motor 21 or between the driver 32b and the left/right motor 22, thereby overheating the switch to turn it off. This protects the up/down motor 21 or the left/right motor 22 against exposure to excessive currents.

Figure 8:
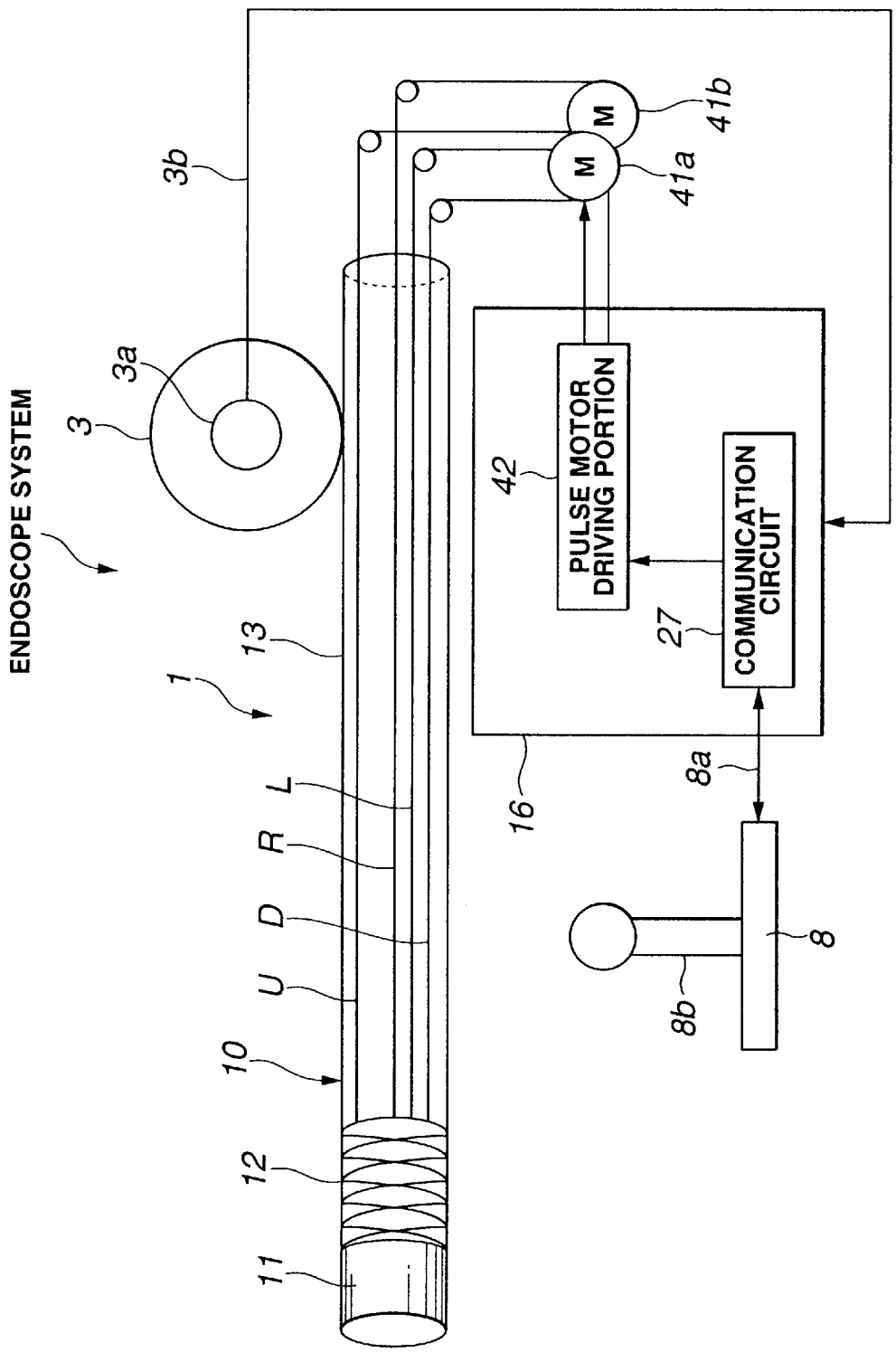
FIG. 8 illustrates another composition of the bending mechanism and control unit of the electrically bendable endoscope.

A variant of the embodiment will now be described with reference to FIG. 8.

Although in the above embodiment the up/down motor 21 is combined with the up/down potentiometer 23 and the left/right motor 22 with the left/right potentiometer 24, as shown in the figure, those motors may be substituted for up/down and left/right pulse motors 41a and 41b respectively, and instead of the motor control unit 25 may be introduced a pulse motor control portion 42 which is electrically connected to the up/down and left/right pulse motors 41a and 41b, thereby dispensing with the use of the A/D converter 26.

According to this configuration, instead of the feedback control which is based on a digital value representing a bent angle of the bendable portion 12 obtained by feeding a detection value from the up/down potentiometer 23 or from the left/right potentiometer 24 to the A/D converter 26, introduced is a feedforward control which is based on the number of pulses applied to the up/down pulse motor 41a or to the left/right pulse motor 41b. Other operations necessary for bending the bendable portion are similar to those of the foregoing embodiment.

As is obvious from above, the present invention is not limited to the electrically bendable endoscope system based on a feedback control dependent on potentiometers or on encoders. Even the electrically bendable endoscope system incorporating pulse motors and devoid of a feedback mechanism can attain the same purpose.

A second embodiment of this invention will be described with reference to FIGS. 9 and 10.

The endoscope system of this embodiment is so configured as to prevent a driving voltage applied to the motor from becoming too large, or a too much strain from being imposed to the bending wire, which would otherwise occur if the joystick is moved so quickly that the processing capability of the control unit can not catch up with the movement, and the difference between a bending instruction from the joystick and the driving voltage applied to the involved motor becomes too large, or to prevent the bendable portion from being subject to fluctuations, even when manipulation of the joystick is fluctuated and thus a bending instructed value therefrom is also fluctuated in association.

Figure 9:
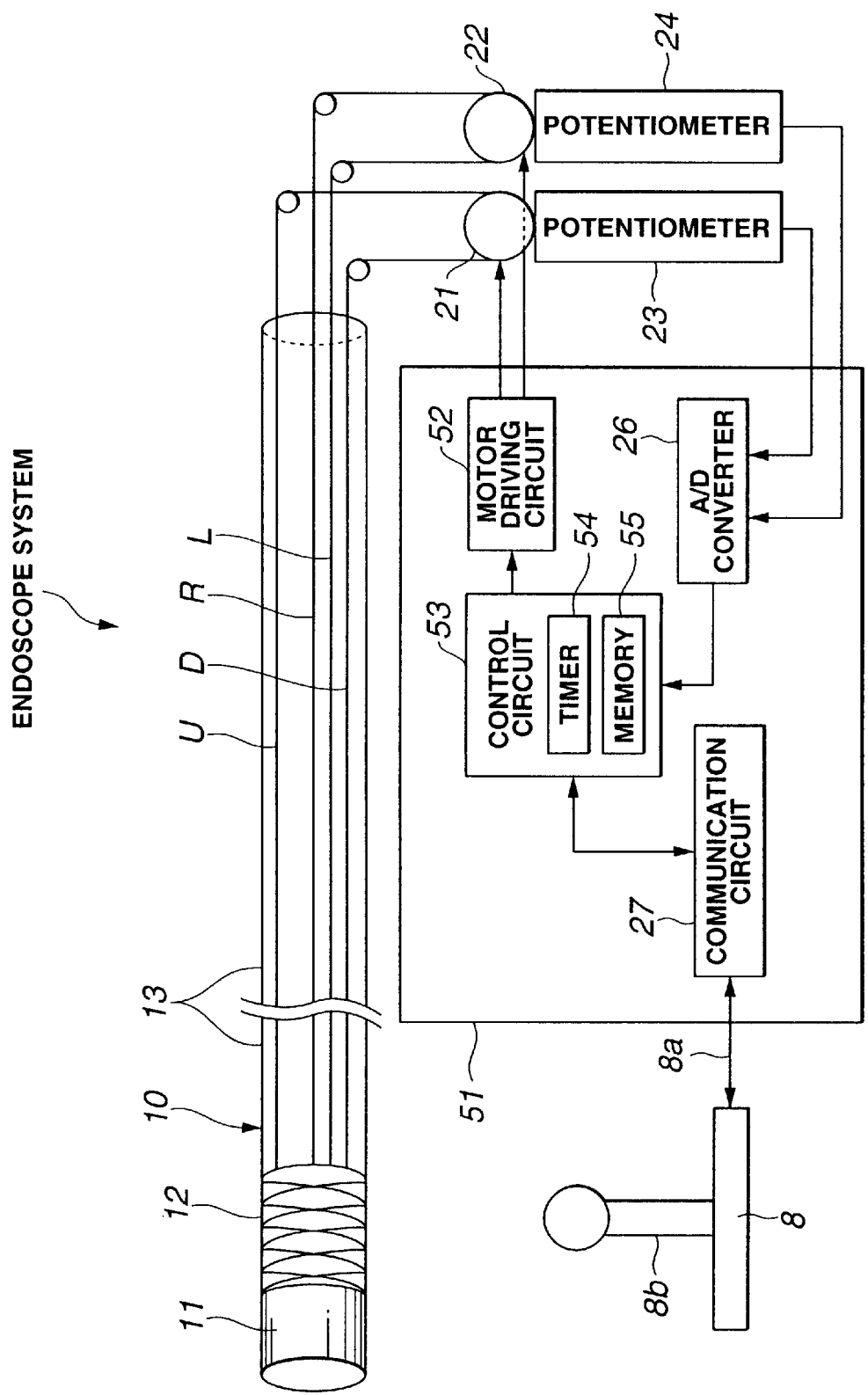
FIGS. 9 and 10 illustrate a second embodiment of this invention.

Thus, according to the present embodiment, as shown in FIG. 9, the control unit 51 consists of a control circuit 53 which comprises a motor driving circuit 52 for driving/controlling the motors 21 and 22, A/D converter 26, and communication circuit 27, and a timer 54 and memory 55 which controls the motor driving circuit 52 based on a difference between an operation instruction signal fed via the joystick 8b and a digital value representing the bending detected by the potentiometer 23 or 24.

The timer 54 introduced in the control circuit 53 is for recording time spent for manipulating the joystick 8b, and the memory 55 is temporary memory means for storing a motor control software program for controlling the motor driving circuit 52 according to steps as depicted in the flow chart of FIG. 10 described later, and various computation results and conditions introduced to be utilized by the motor control software program.

According to this embodiment, when the joystick 8b is manipulated, an operation instruction signal fed via the joystick 8b is captured at predetermined regular intervals. Then, based on the difference between the captured instructed bending amount fed via the joystick 8b and the corresponding digital value digitalized by the A/D converter 26 of the potentiometer 23 or 24, driving force applied to the motor 21 or 22 is controlled at the predetermined regular intervals. Namely, the bending amount of the bendable portion 12 is controlled at regular intervals.

Specifically, as long as the joystick 8b is manipulated by the user, the control circuit 53 of this embodiment captures at predetermined regular intervals, for example, at 10 ms intervals, a bending instruction signal fed via the joystick 8b. Then, the motor control processing is performed according to the procedures as depicted in the flowchart of FIG. 10. The control circuit 53 does not directly employ a bending amount instructed via the joystick 8b as a value based on which an appropriate driving voltage to be applied to the motor 21 or 22 is determined by calculation, but uses the bending amount instructed based on a bent amount via the joystick 8b for correcting and altering the driving voltage to be applied to the motors.

Figure 10:
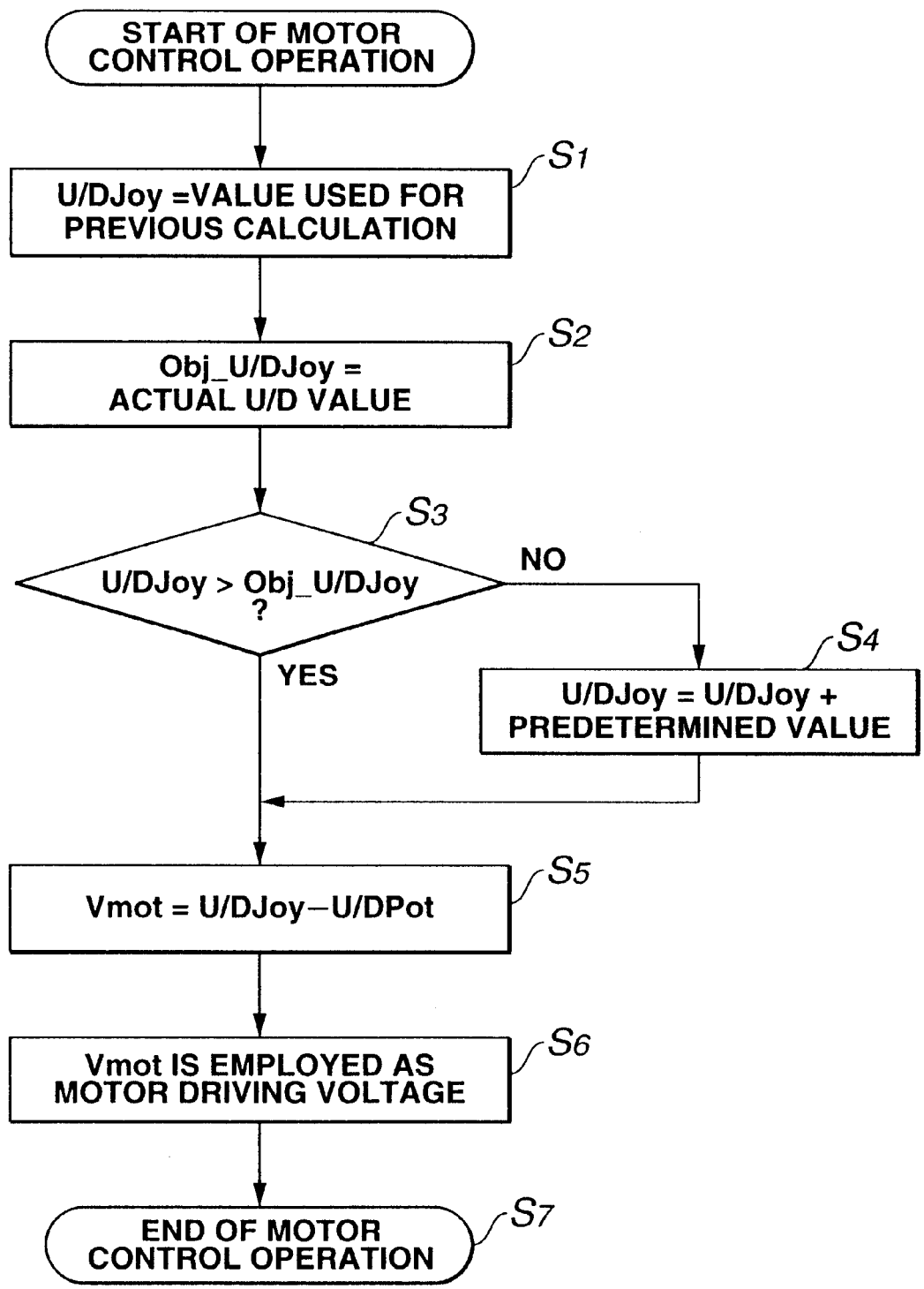

The operation represented in the flowchart of FIG. 10 necessary for the control of the motors shows a flow of the steps taken by the control circuit 53 when the joystick 8b is manipulated in upward/downward directions. The operation is the same when the joystick 8b is manipulated in leftward/rightward directions, except the direction of bending. Thus, after reference being made to this figure, the explanation of the latter operation will be omitted.

Control effected by the control circuit 53 will be described with reference to FIG. 10.

As step S1 shows, the control circuit 53 substitutes a predetermined value used in the previous calculation for a U/DJoy value representing a up/down bending amount in order to run the program.

Next, as step S2 shows, the control circuit defines an obj_U/DJoy as a bending amount in an up/down direction instructed via the joystick 8b, captures instructed bending amount fed via the joystick 8b at predetermined regular intervals, and proceeds to step S3.

At step S3, the control circuit compares the U/DJoy value with the Obj_U/DJoy value or the captured instructed bending value fed via the joystick 8b to check which is the larger. As a result of the comparison, if the U/DJoy is found to be smaller than the obj_U/DJoy, the control circuit proceeds to Step S4, and increases the U/DJoy value by a predetermined amount. This process is repeated until the U/DJoy value becomes equal to the obj_U/DJoy value.

Namely, through this process, it is possible to cause the U/DJoy amount which serves as a value for the actual control here concerned to be altered later than the alteration of the Obj_U/DJoy value or the value representing the instructed bending amount fed via the joystick 8b. This prevents the up/down motor 21 from being exposed to an extremely large motor driving voltage.

Then, as step S5 shows, a Vmot value, the difference between the altered U/DJoy value and a U/DPot or a digital value representing a current bent state of the up/down potentiometer 23 obtained via the A/D converter 26, is determined by calculation.

Then, as step S6 shows, the Vmot value thus determined is multiplied by a factor such as 1/k (positional difference), so that the position value may be transformed into a voltage value which is used as a driving voltage for driving the motor at predetermined time units.

Then, the control circuit 53 outputs the driving voltage to the motor driving circuit 52. The motor driving circuit 52 controls the driving of the up/down motor 21 at the predetermined time units based on the motor driving voltages provided by the control circuit 53. The motor driving circuit 52 causes the bendable portion 12 to be bent at the predetermined time units, and the motor control operation is ended.

Namely, the control circuit 53 repeats the above motor control operation at predetermined regular intervals to control bending at predetermined time units as long as the joystick 8b is manipulated.

As discussed above, because as long as the joystick is manipulated, that is, from the start of joystick manipulation to its end, the bendable portion is bent at predetermined time intervals, it is possible to prevent the occurrence of extremely large motor driving voltages.

Further, because an actual bent state of the bendable portion is compared with an instructed bending amount fed via the joystick which defines a target bending position, and the difference is used for altering the bending speed of the bendable portion, it is possible to easily arrest the bending movement as soon as the target position is reached.

Still further, when an actual bent state of the bendable portion is compared with an instructed bending amount to deduce the difference, the instructed bending amount is altered at predetermined regular intervals. Therefore, it is possible not only to prevent the bendable portion from being exposed to extremely large driving forces during bending, thereby protecting the wires U, D, R and L against excessive strains, but also to relieve the bendable portion from fluctuations in bending and ensures the improved visibility of the target site, even when the manipulation of the joystick is fluctuated and the position to be targeted is fluctuated in association.

Incidentally, the motor control operation will be achieved in the same manner even if the potentiometers 23 and 24 are substituted for encoders, and input from the encoders is directly fed to the control circuit 53 without the intervention of the A/D converter 26.

Notifying means which informs the user of the values detected by the potentiometers 23 and 24 may be added, so that the actual bending amount can be transmitted to the user.

Notifying means not illustrated here may be added to warn the user whenever the bendable portion 12 does not reach a target position specified by an instructed bending amount fed by the joystick 8b within a predetermined interval. Such notifying means may warn the user whenever the risk of a too much strain being inflicted onto the wire U, D, R or L is imminent.

Although, with this embodiment, a motor control operation software program stored in the memory 55 of the control circuit 53 is used for bending the bendable portion 12 at predetermined regular intervals, the present invention is not limited to this mode of operation. A hardware component such as a control circuit capable of achieving the same operation may be employed for controlling the bending in question.

FIG. 11 shows a variant of the second embodiment of this invention.

With the second embodiment, this invention is applied to the electrically bendable endoscope 1 working on a feedback mechanism based on the potentiometers 23 and 24, or on encoders. According to this embodiment, however, pulse motors not based on a feedback mechanism are employed. Because this variant has practically the same configuration as that of the second embodiment, the corresponding members will be represented by the same symbols, and their explanation omitted.

As shown in the figure, the endoscope system of this embodiment incorporates an up/down pulse motor 41a and a left/right pulse motor 41b, in place of the motors 21 and 22, and the potentiometers 23 and 24 of the second embodiment. A control unit 51A includes a pulse motor driving circuit 56 for driving the pulse motors 41a and 41b, instead of the motor driving circuit 52.

The pulse motor driving circuit 56 delivers a certain number of pulses via the control circuit 53 to the pulse motors 41a and 41b so as to control the driving of the motors. The control circuit 53 controls the driving of the motors in a feedfoward manner based on the number of pulses transmitted to the pulse motor driving circuit 56, and thus does not require the use of an A/D converter.

Based on a motor control operation software program stored in a memory 55, the control circuit 53 achieves practically the same control as in the motor control operation described above with respect to the second embodiment: it repeats the delivery of controlled voltages at predetermined regular intervals as long as a joystick 8b is manipulated.

Because this embodiment is based on feedforward control, its motor control operation depends, when described in terms of the steps of FIG. 10, on the number of pulses to be applied to the up/down pulse motor 41a or to the left/right pulse motor 41b, instead of U/DPot of step S5. Other control steps required for the normal bending of the bendable portion are the same with those of the second embodiment.

This variant embodiment of the present invention can ensure the same effects and advantages as does the second embodiment, by applying the present invention to an electrically bendable endoscope connected to pulse motors having no feedback mechanism.

Having described the preferred embodiments of the invention referring to the accompanying drawings, it should be understood that the present invention is not limited to those precise embodiments, and that various changes and modifications thereof could be made by one skilled in the art without departing from the spirit and scope of the invention as defined in the appended claims.

What is claimed is:

1. An endoscope system, comprising:
   an electrically bendable endoscope in which a bendable portion is electrically bendable;
   bending input feeding means for giving an instruction as to a bending amount which includes a bending direction and a bending position which the bendable portion of the electrically bendable endoscope should take as a result of bending;
   driving means for bending the bendable portion based on the bending instruction signal from the bending input feeding means;
   detection means for detecting a bent state of the bendable portion;
   first driving power generating means which obtains a difference between the instructed bending amount given by the bending input feeding means and a value representing the bent state given by the detection means, and generates power for driving the driving means which is responsible for bending the bendable portion in accordance with the difference;
   second driving power generating means for generating a pulse driving power having a predetermined magnitude; and control means whose control includes selecting one of the first and second driving power generating means which have a characteristic of power generating activities according to said difference, and activating the thus selected driving power generating means so as to bend the bendable portion.

2. The endoscope system according to claim 1, wherein:

the control means switches a driving voltage applied to the driving means from a normal voltage to a pulse voltage according to said difference.

3. The endoscope system according to claim 1, further comprising:

winding means for taking up an insertion portion of the electrically bendable endoscope to hold it;

detection means for detecting an amount of the insertion portion which is wound around the winding means for winding; and correction means for correcting a driving power generated by the first or second driving power generating means according to a detection result given by the detection means, wherein:

the control means controls such that the driving means bends the bendable portion with the driving power corrected by the correction means.

4. The endoscope system according to claim 3, wherein:

the control means corrects driving voltage in accordance with an amount of the insertion portion wound up around the winding means in such a manner as to keep the bending amount of the bendable portion constant regardless of the wound-up amount of the insertion portion.

5. The endoscope system according to claim 3, wherein:

the control means prevents driving voltage from becoming equal to or higher than a predetermined value which would otherwise occur depending on the amount of the insertion portion wound up around the winding means.

6. The endoscope system according to claim 3, wherein:

the magnitude of a pulse voltage is corrected in accordance with the amount of the insertion portion wound up around the winding means.

* * * * *